United States Patent [19]

Cannata et al.

[11] Patent Number: 5,057,624

[45] Date of Patent: Oct. 15, 1991

[54] PROCESS FOR THE SYNTHESIS OF THE N-METHYL-3,4-DIMETHOXYPHENYLE-THYLAMINE

[75] Inventors: Vincenzo Cannata; Giancarlo Tamerlani; Graziano Zagnoni, all of Bologna, Italy

[73] Assignee: ALFA Wassermann S.p.A., Prescara, Italy

[21] Appl. No.: 502,038

[22] Filed: Mar. 30, 1990

[30] Foreign Application Priority Data

Mar. 31, 1989 [IT] Italy ................................ 19959 A/89

[51] Int. Cl.⁵ .......................................... C07C 209/28
[52] U.S. Cl. ..................... 564/375; 549/513; 549/519; 564/374; 564/384; 564/385; 564/389; 568/435
[58] Field of Search ............... 564/374, 375, 384, 385, 564/389; 549/519, 513; 568/435

[56] References Cited

U.S. PATENT DOCUMENTS 3,894,051 7/1978 Suh ................................ 564/375 X
3,997,608 12/1976 Suh ................................ 564/375 X

FOREIGN PATENT DOCUMENTS 233762 8/1987 European Pat. Off. .
3338681 5/1985 Fed. Rep. of Germany .

OTHER PUBLICATIONS

The Merck Index, 10th Edition, "Darzens Condensation" p. ONR-22(1983).
M. S. Newman and B. J. Magerlein (1949) in *Organic Reactions*, vol. V, p. 413.
*The Merck Index* (1983) Tenth Ed., Merck and Co., Inc., Rahway, N.J., p. 864.
Aldrich Chemical Catalogue (1990–1991), pp. 490, 494 and 495.
Chemical Abstracts, vol. 87, 1977, Abstract No. 87:134467n.

*Primary Examiner*—Richard L. Raymond
*Attorney, Agent, or Firm*—Birch, Stewart, Kolasch & Birch

[57] ABSTRACT

New process for the synthesis of the N-methyl-3,4-dimetoxyphenylethylamine of formula

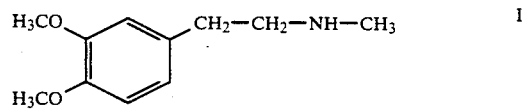

intermediate in the synthesis of the drug internationally known as verapamil. The process starts from the 3,4-dimethoxybenzaldehyde which, by means of a Darzens condensation, gives an epoxyester that, by alkaline hydrolysis and subsequent decarboxylation, gives the 3,4-dimethoxyphenylacetaldehyde. This aldehyde gives the amine of formula I by reaction with monomethylamine followed by reduction with sodium borohydride.

7 Claims, No Drawings

PROCESS FOR THE SYNTHESIS OF THE N-METHYL-3,4-DIMETHOXYPHENYLETHYLAMINE

BACKGROUND OF THE INVENTION

The N-methyl-3,4-dimethoxyphenylethylamine, also known under the name of N-methylomoveratrylamine, is an intermediate useful in the synthesis of a drug having coronarodilator activity, internationally known as verapamil (INN), described in the U.S. Pat. No. 3,261,859.

The synthesis of the N-methylomoveratrylamine was described both in patent documents like the unexamined japanese publication JP 77036606, the german publication DE 3338681 and the european publication EP 0233766 and in scientific publications, for instance in J. Med. Chem. 16, (6), 630–3, (1973), in J. Am. Chem. Soc. 104, (3), 877–9 (1982) and in J. Org. Chem. 52, (7), 1309–15, (1987).

In the japanese publication, the N-methylomoveratrylamine is obtained by reducing the corresponding amide by means of a mixture made by an organic acid and by sodium borohydride.

In the german publication, the veratrylcyanide is catalytically hydrogenated, by using a nickel catalyst, in the presence of a strong molar excess (10:1) of methylamine.

In the european publication EP 0233762, the N-methylomoveratrylamine is obtained by acylating the omoveratrylamine with methyl chloroformate and then by reducing the so obtained compound by means of a molar excess of lithium aluminium hydride in anhydrous tetrahydrofuran.

DESCRIPTION OF THE INVENTION

The object of the present invention is a new method for the synthesis of the N-methyl-3,4-dimethoxyphenylethylamine of formula

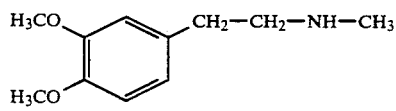
I also known as N-methylomoveratrylamine, starting from the 3,4-dimethoxybenzaldehyde of formula

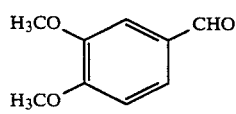
II also known as veratraldehyde, which is submitted to the Darzens condensation by means of an alkyl ester of an α-haloacetic acid, in the presence of an alcoholate of an alkali metal or of sodium amide or sodium hydride, to give an α,β-epoxyester of formula

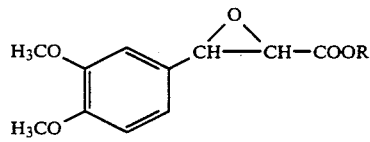
III wherein R represents an alkyl radical, straight or branched, containing from 1 to 6 carbon atoms, which by alkaline hydrolysis gives the alkaline salt of the epoxyacid of formula

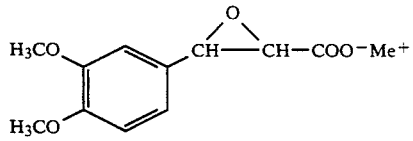
IV wherein Me+ corresponds to a cation of an alkaline metal, preferably sodium or potassium, which by decarboxylation gives the 3,4-dimethoxy-benzeneacetaldehyde of formula

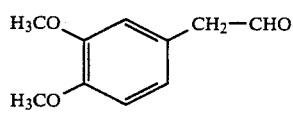
V which by treatment first with monomethylamine and then with sodium borohydride furnishes the N-methyl-3,4-dimethoxyphenylethylamine of formula I.

The process object of the present invention is advantageously carried out without isolating and characterizing the various intermediates of the above formulae: however, if it is wanted, the various steps of this process can also be carried out one by one, by isolating and characterizing the relating intermediates.

The process object of the present invention consists in reacting one mole of 3,4-dimethoxybenzaldehyde of formula

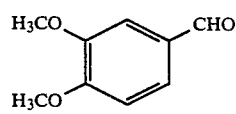
II with from about 1 to about 4 moles of an α-halo-ester of formula

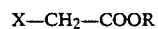
VI wherein X represents a halogen atom, preferably a chlorine atom, and R represents an alkyl radical, straight or branched, containing from 1 to 6 carbon atoms, preferably methyl, ethyl or 2-butyl, in the presence of from about 1 to about 4 moles of a base selected among an alcoholate of an alkaline metal of formula

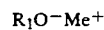
VII wherein Me+ represents the cation of an alkaline metal, preferably sodium or potassium, and R₁ represents an alkyl radical, straight or branched, containing from 1 to 6 carbon atoms, sodium amide or sodium hydride. Sodium methoxide, potassium tert-butoxide, sodium 2-butoxide, potassium 2-butoxide and potassium n-propoxide are the bases preferably used. The reaction takes place in a period of time comprised between about 1 and about 6 hours at a temperature comprised between about 0° C. and about 40° C. The reaction can take place with or without solvents; the aromatic hydrocarbons, preferably toluene, and the straight or branched alcohols containing from 1 to 6 carbon atoms, preferably 2-butanol, or mixtures thereof, showed to be suitable solvents.

The glycidic ester of formula

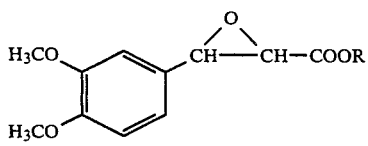

which forms during the reaction, wherein R has the above seen meaning, generally is not isolated but it is transformed into the alkaline salt of the epoxyacid of formula

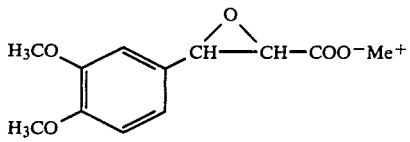

wherein Me+ corresponds to a cation of an alkaline metal, preferably sodium or potassium, through an alkaline hydrolysis carried out by treating the solution containing the epoxyester of formula III with an aqueous solution of sodium or potassium hydroxide, for a period of time comprised between about 6 and about 24 hours, at a temperature comprised between about 10° C. and about 40° C.

The salt of the epoxyacid of formula IV is then decarboxylated in acidic medium, preferably in the presence of monopotassium phosphate, at a temperature comprised between about 10° C. and about 40° C., for a period of time comprised between about 1 and about 8 hours. In this way the 3,4-dimethoxybenzeneacetaldehyde of formula

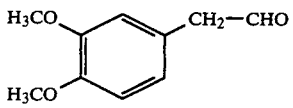

is obtained, which by reaction with from about 1 to about 6 moles of an aqueous solution of monomethylamine, at a temperature comprised between about −10° C. and about 40° C. for a period of time comprised between about 1 and about 6 hours and a subsequent treatment with from about 0.5 to about 1 moles of sodium borohydride at a temperature comprised between about −10° C. and about 80° C. for a period of time comprised between about 2 and about 8 hours, gives the desired N-methyl-3,4-dimethoxyphenylethylamine of formula I.

The so obtained raw product can be purified either by distillation under vacuum or by crystallization of the hydrochloride obtained dissolving the product in a suitable solvent or solvent mixture and treating the solution with gaseous hydrochloric acid.

The examples below reported constitute an illustration of the present invention and are not to be taken as a limitation of it.

EXAMPLE 1

N-methyl-3,4-dimethoxyphenylethylamine 948.4 Ml of a 14.57% (w/v) solution of potassium 2-butoxide (1.23 moles) in 2-butyl alcohol are poured under stirring in about one hour into a solution of 166.2 g (1 mole) of 3,4-dimethoxybenzaldehyde in 205 ml (1.44 moles) of 2-butyl chloroacetate, while keeping the temperature between 15° C. and 20° C. The reaction mixture is kept at room temperature under stirring for another hour and then it is added in about 2 hours to a solution containing 93 g of 90% potassium hydroxide (1.49 moles) in 130 ml of water while keeping the temperature between 15° C. and 20° C. The reaction mixture is kept under stirring at this temperature for three hours, then it is left standing for 12 hours at room temperature and lastly it is cooled to 10° C. and filtered. The solid is washed with 150 ml of 2-butyl alcohol and then with 300 ml of methylene chloride and subsequently it is added portionwise to a mixture made by 500 ml of water, 500 ml of methylene chloride and 140 g of monopotassium phosphate while keeping the reaction mixture under stirring for about 2 hours at room temperature. The two layers are then separated, the aqueous phase is twice extracted with 50 ml of methylene chloride and then it is discarded, while the organic layers are collected, washed with 100 ml of water and dripped under strong stirring on 296 ml of a 33.1% (w/v) aqueous solution of monomethylamine (3.15 moles) while keeping the temperature at about −5° C. for about 2 hours. The layers are separated after addition of 4 g of sodium chloride, the aqueous layer is extracted three times with 50 ml of methylene chloride and then it is discarded while the organic layers are collected and added with 500 ml of methyl alcohol.

The mixture is added, in about one hour, with a solution containing 18.90 g (0.50 moles) of sodium borohydride in 188 ml of water containing 2 drops of a 15% (w/v) aqueous solution of sodium hydroxide while keeping the temperature between 0° C. and 5° C. The reaction mixture is kept under stirring for other 2 hours at a temperature comprised between 0° C. and 10° C. and then is added with 100 ml of a 30% (w/v) aqueous solution of sodium hydroxide and with 500 ml of water. The layers are separated, the aqueous layer is extracted three times with 100 ml of methylene chloride and then is discarded, while the organic layers are collected, washed with 250 ml of water and then are added first with 700 ml of water and then with 114 ml of 86% (w/v) sulfuric acid. The layers are separated, the organic layer is twice extracted with 100 ml of water and then is discarded, while the aqueous layers are collected, added with 600 ml of toluene and 220 ml of a 30% (w/v) aqueous solution of sodium hydroxide. The layers are separated and the aqueous layer is extracted three times with 100 ml of toluene and then is discarded, while the organic layers are collected, dried on anhydrous sodium sulfate and evaporated under vacuum to give 173.5 g of raw product.

The raw product is purified by distillation under vacuum, collecting the portion which distils between 122° C. and 127° C. under a pressure of about 2 mm of mercury. 149.4 Grams of pure product having a HPLC title of 98% are obtained with a yield equal to 76.5% calculated over the starting 3,4-dimethoxybenzaldehyde.

EXAMPLE 2

N-Methyl-3,4-dimethoxyphenylethylamine hydrochloride

910 Ml of a 15.15% (w/v) solution of potassium 2-butoxide (1.23 moles) in 2-butyl alcohol are added under stirring in about 2 hours to a solution containing 166.2 g (1 mole) of 3,4-dimethoxybenzaldehyde in 210 ml (1.48 moles) of 2-butyl chloroacetate while keeping the temperature at about 15° C.

The reaction mixture is kept under stirring at room temperature for further 30 minutes and then is added in 45 minutes with 50 ml of water and in 90 minutes with a solution containing 92 g of 85% potassium hydroxide in 75 ml of water while keeping the temperature at about 20° C. The reaction mixture is kept under stirring at about 20° C. for 15 hours and then it is filtered; the solid is added portionwise under stirring in about one hour to a mixture made by 500 ml of toluene, 500 ml of water, 67.8 g of 85% potassium hydroxide and 70 ml of 85% (w/w) phosphoric acid, while keeping the temperature at about 20° C. and going on with the stirring at this temperature for further two and half hours.

The layers are separated and 175 ml of a 40% (w/v) aqueous solution of monomethylamine (2.25 moles) are added under stirring in about one hour to the organic layer while keeping the temperature at about 10° C. The reaction mixture is kept under stirring at this temperature for another hour and half, then it is cooled to about 5° C., added with 150 ml of methanol, further cooled to −5° C. and added in about one hour with an aqueous solution containing 18.90 g (0.50 moles) of sodium borohydride in 39 ml of water containing 2 drops of a 30% (w/v) aqueous solution of sodium hydroxide. The reaction mixture is kept under stirring another hour at −5° C., then in one hour the temperature is brought to 25° C. The reaction mixture is kept at this temperature for one hour, at 40° C. for one hour, at 50° C. for one hour and at 68° C. for another hour. Subsequently, 250 ml of water are added to the reaction mixture and the layers are separated. The aqueous layer is twice extracted with 60 ml of toluene and then is discarded, the organic layers are collected and added with 250 ml of water and 100 ml of 32% (w/v) aqueous hydrochloric acid. The layers are separated after 30 minutes, the organic layer is discarded while the aqueous layer is concentrated under vacuum until elimination of the methanol present, then it is twice washed with 100 ml of methylene chloride, put again under vacuum in order to eliminate the traces of the organic solvent and lastly added with 240 ml of toluene and 100 ml of a 30% (w/v) aqueous solution of sodium hydroxide. The two layers are separated, the aqueous layer is twice extracted with 80 ml of toluene and then is discarded. The toluene layers are collected and evaporated under vacuum to give a residue which is dissolved in a mixture made by 480 ml of acetone and 24 ml of water. Gaseous hydrochloric acid is added until acidic pH to the resulting solution which subsequently is cooled under stirring to 5° C. for one hour and the resulting suspension is filtered. The solid on the filter is washed with acetone and dried in oven under vacuum.

159 Grams of N-methyl-3,4-dimethoxyphenylethylamine hydrochloride are obtained with a yield of 69% calculated over the starting 3,4-dimethoxybenzaldehyde.

EXAMPLE 3

N-Methyl-3,4-dimethoxyphenylethylamine hydrochloride

The product is prepared according to the same conditions and amounts referred to in example 2, by using the 1,1,1-trichloroethane as solvent instead of the toluene.

152 Grams of product are obtained with a yield o 66% calculated over the starting 3,4-dimethoxybenzaldehyde.

EXAMPLE 4

N-Methyl-3,4-dimethoxyphenylethylamine hydrochloride 948.4 Ml of a 14.57% (w/v) solution of potassium 2-butoxide (1.23 moles) in 2-butyl alcohol are added under stirring in about one hour to a solution of 166.2 g (1 mole) of 3,4-dimethoxybenzaldehyde in 205 ml (1.44 moles) of 2-butyl chloroacetate while keeping the temperature between 15° C. and 20° C. The reaction mixture is kept under stirring for another hour at room temperature and then is added in about 2 hours to a solution containing 93 g of 90% potassium hydroxide (1.49 moles) in 130 ml of water while keeping the temperature between 15° C. and 20° C. The reaction mixture is kept under stirring at room temperature for 15 hours and then is added in about one hour to a mixture made by 780 ml of water, 109.2 ml of 85% (w/w) phosphoric acid, 99.84 g of 90% potassium hydroxide and 100 ml of toluene, keeping the reaction mixture under stirring at about 20° C. for another hour. Subsequently the layers are separated, the aqueous layer is extracted with 50 ml of toluene and then is discarded, while the organic layers are collected, washed with 100 ml of a 10% (w/v) aqueous solution of anhydrous sodium sulfate and added under stirring to 300 ml of a 33.1% (w/v) aqueous solution of monomethylamine (3.19 moles) while keeping the temperature between 10° C. and 15° C.

The reaction mixture is kept under these conditions for one hour, then it is cooled until 0° C. in one hour and is added with an aqueous solution containing 18.90 g (0.5 moles) of sodium borohydride in 39 ml of water alkalinized with two drops of a 30% (w/v) aqueous solution of sodium hydroxide. The reaction mixture is kept one hour at 0° C. under stirring and subsequently it is slowly heated till the temperature of about 78° C. A 32% (w/v) aqueous solution of hydrochloric acid is added to the reaction mixture, cooled to room temperature, until pH 2 and then the layers are separated.

The organic layer is discarded, while the aqueous phase is twice washed with 100 ml of methylene chloride, then it is added with 250 ml of toluene and brought to alkaline pH by adding 100 ml of a 30% (w/v) aqueous solution of sodium hydroxide.

The layers are separated, the aqueous layer is twice extracted with 100 ml of toluene and then is discarded, while the toluene solutions are collected and evaporated under vacuum giving a residue which is dissolved in a mixture of 480 ml of acetone and 24 ml of water where gaseous hydrochloric acid is bubbled till acidic pH. The suspension, after one hour of cooling to 5° C. under stirring, is filtered and the obtained solid is washed with acetone and dried in oven under vacuum.

145.5 Grams of pure product are obtained with a yield of 63% calculated over the starting 3,4-dimethoxybenzaldehyde.

We claim:

1. A new chemical process for the synthesis of the N-methyl-3,4-dimethoxyphenylethylamine of formula

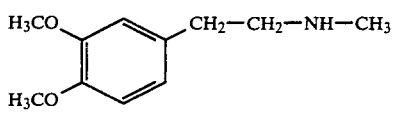  I which comprises:
a) reacting the 3,4-dimethoxybenzaldehyde of formula

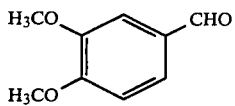  II with an α-haloester of formula

X—CH$_2$—COOR     VI wherein X represents a halogen atom and R represents an alkyl radical, straight or branched, containing from 1 to 6 carbon atoms, in the presence of an alkaline agent selected among an alcoholate of an alkaline metal of formula R$_1$O$^-$Me$^+$     VII wherein Me$^+$ represents the cation of an alkaline metal, and R$_1$ is an alkyl radical, straight or branched, containing from 1 to 6 carbon atoms, sodium amide or sodium hydride, optionally in the presence of a solvent selected between an aromatic hydrocarbon and an alcohol, straight or branched, containing from 1 to 6 carbon atoms, or mixtures thereof, for a period of time comprised between about 1 and about 6 hours at a temperature comprised between about 0° C. and about 40° C.
b) submitting the resulting glycidic ester of formula

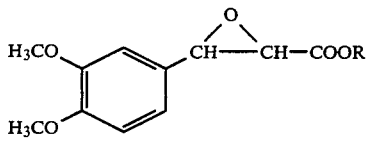  III wherein R has the above seen meaning, to an alkaline hydrolysis at a temperature comprised between about 10° C. and about 40° C. for a period of time comprised between about 6 and about 24 hours, to obtain an alkaline salt of the epoxyacid of formula

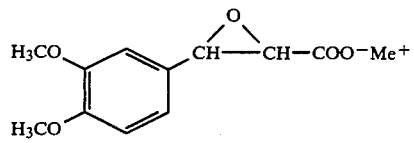  IV wherein Me$^+$ has the above seen meaning;
c) decarboxylating the compound of formula IV in acidic ambient, at a temperature comprised between about 10° C. and about 40° C., for a period of time comprised between about 1 and about 8 hours, to obtain the 3,4-dimethoxybenzeneacetaldehyde of formula

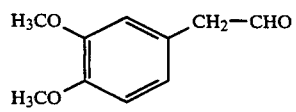  V d) treating said aldehyde of formula V first with monomethylamine at a temperature comprised between about −10° C. and about 40° C., for a period of time comprised between about 1 and about 6 hours, and subsequently with sodium borohydride at a temperature comprised between about −10° C. and about 80° C., for a period of time comprised between about 2 and about 8 hours, to obtain the N-methyl-3,4-dimethoxyphenylethylamine of formula I.

2. A process as defined in claim 1 wherein for each mole of 3,4-dimethoxybenzaldehyde from about 1 to about 4 moles of an α-haloester of formula VI and from about 1 to about 4 moles of a base selected from an alkaline alcoholate of formula VII, sodium amide and sodium hydride are used.

3. A process as defined in claim 1 wherein the α-haloester of formula VI is selected among the methyl chloroacetate, the ethyl chloroacetate and the 2-butyl chloroacetate.

4. A process as defined in claim 1 wherein the alcoholate of formula VII is selected among the sodium methoxide, the potassium 2-butoxide, the sodium 2-butoxide, the potassium tert-butoxide and the potassium n-propoxide.

5. A process as defined in claim 1 wherein the solvent used to obtain the glycidic ester of formula III is the 2-butanol.

6. A process as defined in claim 1 wherein the decarboxylation takes place in the presence of monopotassium phosphate.

7. A process as defined in claim 1 wherein from about 1 to about 6 molar equivalents of monomethylamine in aqueous solution are used.

* * * * *